(12) United States Patent
Levinson

(10) Patent No.: US 6,890,344 B2
(45) Date of Patent: May 10, 2005

(54) HEMOSTASIS PAD AND METHOD

(75) Inventor: Melvin Levinson, Pinecrest, FL (US)

(73) Assignee: Scion Cardiovascular, Inc., Miami, FL (US)

( * ) Notice: Subject to any disclaimer, the term of this patent is extended or adjusted under 35 U.S.C. 154(b) by 0 days.

(21) Appl. No.: 10/286,566

(22) Filed: Nov. 1, 2002

(65) Prior Publication Data

US 2003/0093115 A1 May 15, 2003

Related U.S. Application Data

(63) Continuation-in-part of application No. 10/008,052, filed on Nov. 13, 2001.

(51) Int. Cl.$^7$ .......................... A61B 17/04; A61F 13/00
(52) U.S. Cl. ............................ 606/213; 602/43; 602/48
(58) Field of Search ............................... 606/151, 213, 606/214; 602/43, 48

(56) References Cited

U.S. PATENT DOCUMENTS

| | | | |
|---|---|---|---|
| 3,811,438 A | | 5/1974 | Economou et al. |
| 4,394,373 A | | 7/1983 | Malette et al. |
| 4,784,653 A | * | 11/1988 | Bolton et al. ................. 602/54 |
| 4,833,238 A | | 5/1989 | De Lucca et al. |
| 5,086,764 A | * | 2/1992 | Gilman ......................... 602/42 |
| 5,429,591 A | * | 7/1995 | Yamamoto et al. ............ 602/54 |
| 5,533,962 A | * | 7/1996 | Peterman et al. ............. 602/54 |
| 5,683,354 A | * | 11/1997 | Levy ............................. 602/54 |
| 5,836,970 A | | 11/1998 | Pandit |
| 5,985,434 A | | 11/1999 | Qin et al. |
| 6,060,461 A | | 5/2000 | Drake |
| 6,316,686 B1 | * | 11/2001 | Byrd ............................. 602/41 |
| 6,586,651 B2 | * | 7/2003 | Sullivan ....................... 602/58 |
| 6,638,284 B1 | | 10/2003 | Rousseau et al. |
| 2003/0050589 A1 | * | 3/2003 | McDevitt et al. ............. 602/41 |

OTHER PUBLICATIONS

Vanson Chitin Chitosan and Chitosan Derivatives Entrance: http;//www.vanson.com; Jul. 27, 2001.
Chitin and Chitosan and their Medical Applications; http//www.vanson.com/pages/med/biomed.html; Jul. 27, 2001.
Properties of Chitosan; http://www.vanson.com/pages/med/Properties.html; Jul. 27, 2001.
Properties of Chitosan; http://www.vanson.com/pages/med/solution.html; Jul. 27, 2001.
Physical Forms of Chitosan and their Applications; http://www.vanson.com/pages/med/forms.html; Jul. 27, 2001.
International Search Report (PCT/US02/36564).
International Search Report (PCT/US03/34831).

* cited by examiner

Primary Examiner—Gary Jackson
(74) Attorney, Agent, or Firm—McDermott Will & Emery LLP

(57) ABSTRACT

The present invention relates generally to medical devices for applying hemostatic composition to a puncture or wound site with indwelling tubular element, such as catheter, introducer or tube therein, particularly a hemostatic pad with an opening therethrough in order to allow egress of the indwelling tubular element through the hemostatic pad as the hemostatic pad provide hemostasis at the hemorrhaging site. The device may be applied to, or removed from, the wound site while the tubular element is in place. A method for effecting hemostasis at a puncture wound, includes applying pressure proximal to the puncture wound, and directing a cationic biopolymer of glucosamine application surface of a closure pad against the puncture wound with force sufficient to prevent fluid from exiting the puncture wound. Then the pressure proximal to the puncture wound is removed and the force on the closure pad is maintained for at least a first predetermined time period. The force on the closure pad is removed if hemostasis is verified. The puncture wound may then be dressed over the closure pad, and the dressing and the closure pad removed after a second predetermined time period.

29 Claims, 4 Drawing Sheets

HEMOSTASIS PAD AND METHOD

REFERENCE TO RELATED APPLICATION

This application is a continuation in part of U.S. patent application Ser. No. 10/008,052, filed Nov. 13, 2001, the disclosure of which is incorporated herein by reference.

FIELD OF THE INVENTION

The present invention relates to medical devices for hemostasis, and methods of using the medical devices for hemostasis. More particularly, the present invention relates to medical devices for effecting hemostasis at a puncture wound with an indwelling tubular element extending therethrough.

BACKGROUND OF THE INVENTION

Puncture of blood vessels is a necessary stage in many of the minimally invasive approaches to diagnosis and treatment, including interventional radiology and cardiology. Therefore, a need to create hemostasis as rapidly as possible following the procedure becomes an important priority.

Various hemostatic agents, such as synthetic or natural cationic polymers, hydrogels, collagen based products, oxidized cellulose, gelatin derivatives, topical thrombin, astringents, vasoconstrictors, etc. have been and are being utilized. Most conventional devices and methods of application are designed as a pad or dressing, incorporating these hemostatic agents to the bleeding site, puncture site or wound site.

Certain medical procedures require insertion of a tubular element, such as catheter, introducer or tube in an artery or other vessel of a patient. The insertion of such tubular element makes it difficult to provide an effective hemostasis at a puncture wound because the hemostatic substances can not be applied quite directly and intimately under pressure to the bleeding or wound site. However, an immediate hemostasis is often needed during surgery while a tubular element is still in the vessels of the patient or after the tubular element is removed. Therefore, what is needed is a simple, safe and effective device and method for providing more directly and intimately hemostasis to the bleeding site with an indwelling tubular element, such as catheter, introducer or tube, and allowing the tubular element to be easily removed thereafter.

SUMMARY OF THE INVENTION

The present invention provides a device and method for effecting hemostasis at a wound site with an indwelling tubular element, such as catheter, introducer or tube disposed therein.

Many hemostasis methods have been utilized or attempted, including suture-based devices, collagen plugs, pressure applying devices, and the like. The situation is complicated further by the use of anticoagulants in these procedures, which prolongs clotting times. Substances such as heparin, aspirin, coumadin, and other anticoagulants are used with regularity and affect the normal blood coagulation cascade. The use of cationic substances in flocculation and coagulation in non-medical situations such as water treatment, paper production, industrial sludge treatment, and the like has been effectively used in the past and is well documented. The method of action is by precipitating, coagulating or flocculating suspended particles which are negatively charged by virtue of using positively charged materials, which attract the oppositely charged ions.

It has been clearly demonstrated that the charge on blood cells and components (platelets, etc.) is negative. By using a positively charged biocompatible substance, it is possible to agglomerate these cells creating coagulation through a system other than by virtue of the normal clotting cascade. Innocuous polymers are positively charged (cationic substances) as the initiator of coagulation in clinical situations. Additionally, positive charges can be applied via iontophoretic methods using electrode pads and positively charged treatment sites to accomplish the same thing.

The use of a positive charge administered by either cationic substances or by iontophoretic means to quickly create a coagulation process and hemostasis until the normal clotting cascade can take over. This can occur even in the face of significant anticoagulation since the process is ionic and not effected by the anticoagulants, which operate on the normal blood cascade. This approach can be revolutionary in the after treatment of patients with minimally invasive or invasive procedures since rapid hemostasis and mobilization of the patient are desirable endpoints.

The cationic substance can be incorporated into many forms, such as woven and non-woven pads, fibers, gels, pastes, waxes, foams, sprays, liquids of varying viscosities, packings, membranes, sheets, and the like. Additionally, these forms can be incorporated and utilized with iontophoretic types of equipment that create a positive charge at the bleeding site to effect coagulation.

Utilizing colloidal chemistry for effecting coagulation ionically in suspensions or colloidal substance by providing cationic charges, has enormous value in the diagnosis and treatment of conditions such as cardiovascular disease, interventional radiological procedures, and the like. The cationic charge can be provided by a substance with a positively charged surface, or electronically by utilizing electrophoretic type equipment and electrode pads specifically designed to be disposable, conductive and sterile, designed to fit the required anatomical site. Many cationic substances are available, such as polymers, polysaccharides and starches, aluminum salts, magnesium salts, natural polymers such as chitosan, and the like.

The use of ionic charges to create hemostasis is a new and important process in the treatment of disease processes. This novel approach can be administered by applying sterile, biocompatible, positively charged materials directly in contact with the blood column, accompanied by pressure, or provided electronically by utilizing controlled direct current on the positive side with iontophoretic type approaches and specially constructed, disposable, sterile electrodes to the bleeding site According to one aspect of the present invention, a hemostatic pad defines an opening at an approximately central point of the pad. The opening is sized to allow egress of the indwelling tubular element through the pad. The pad further comprises an application surface which contains hemostatic agent used for stopping the bleeding at the wound site associated with an indwelling tubular element. The hemostatic agent preferably is a cationic substance, such as cationic polymer, or a cationic protein. The pad, with the indwelling tubular element passing through the opening of the pad, provides an even application of pressure to the wound site. The hemostatic substance on the pad, therefore, may be applied evenly, directly and intimately to the wound site around the tubular element. It also allows the indwelling tubular element to be easily removed from the wound site through the pad. In a preferred embodiment, the opening of the pad is a slit extending from an approximate center to an edge of the pad. In another preferred embodiment, the opening is constructed as an aperture with an elongated cut extending from the aperture to an edge of the pad. In one preferred form, the slit or the elongated cut is at a bias angle with respect to the central region of the pad.

According to another aspect of the present invention, the hemostatic pad may have a non-slip etched area on a top surface of the pad, in order to achieve more friction between the finger of a surgeon and the surface of the pad. The non-slip etched area make it easier to apply a pressure to a puncture site, and make the hemostasis more efficiently and quickly.

The present invention also provides a method for effecting hemostasis at a puncture wound with a pad having an opening sized to allow egress of a tubular element disposed in the puncture wound. The pad may be applied to or removed from the wound while the tubular element is in the wound. The method includes applying pressure proximal to the puncture wound, and directing the application surface, which contains a hemostatically effective amount of cationic substances, of the pad against the puncture wound with sufficient force to prevent fluid from exiting the puncture wound, and permitting the indwelling tubular element going through the pad, removing the pressure on the puncture wound, and maintaining the force on the pad against the wound for a predetermined time period, upon verification (usually visually) of hemostasis, removing the force on the pad.

According to one aspect of the present invention, the application surface of the pad is a biopolymer of glucosamine, including but not limited to poly-N-acetylglucosamine. In some forms of the invention, the application surface is an acetate salt of a biopolymer of glucosamine.

According to further aspect of the present invention, when a tubular element is disposed in the wound, the predetermined time period is substantially proportional to the diameter of the tubular element.

The present invention provides many benefits, including reducing the time period required to stop bleeding at a puncture wound and decreasing the likelihood that a hematoma will form particularly, but not limited to, cases following removal of an introducer, a catheter or a tube from the puncture wound. These and other features and benefits of the present disclosure will become more apparent upon reading the following specification in combination with the accompanying drawing figures.

BRIEF DESCRIPTION OF THE DRAWINGS

Other features and advantages of the present invention will be apparent from the following detailed description of the drawing in which.

DETAILED DESCRIPTION OF THE PREFERRED EMBODIMENTS

The present invention is described hereinafter with specific references to the use of the present invention for sealing an incision or puncture wound with an indwelling tubular element, such as catheter, introducer or tube, through the incision or puncture wound. It is contemplated that the present invention may be used with any catheterization or other medical procedure such as laparoscopic or other minimally or less invasive surgeries wherein it is desirable to seal an incision or puncture wound in the patient to prevent the loss of the patient's body fluid therethrough.

Figure 1:
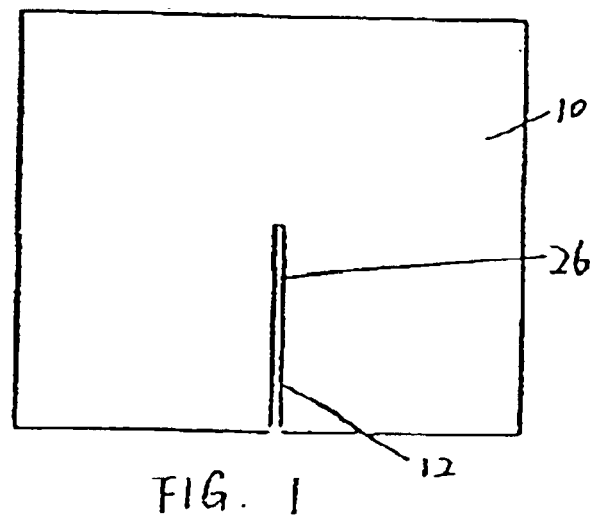
FIG. 1 is a top view of one embodiment of the present invention showing an opening, particularly a slit extending from an approximately central point to an edge of the pad.
Figure 2:
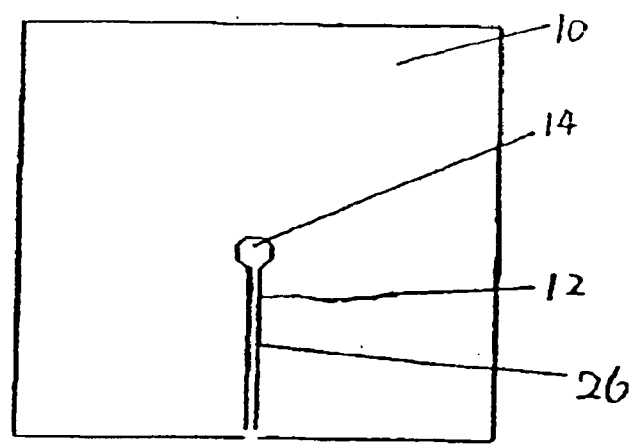
FIG. 2 is a top view of another embodiment of the present invention showing an opening, particularly an aperture at an approximate center of the pad and a slit extending from the aperture to an edge of the pad.

FIG. 1 is a top view of one preferred embodiment of the present inveniton. Referring to FIG. 1, a pad 10 defines an opening 12 through the pad 10. In a preferred embodiment, the opening is constructed as a slit or an elongated cut 26. As shown in FIG. 1, the slit 26 extends from an approximately central point to an edge of the pad 10. The slit is preferably sized to permit egress of an indwelling tubular element, such as catheter, introducer, or tube (not shown) through the pad 10. In another embodiment of the present invention, as shown in FIG. 2., the opening 12 is constructed as a generally circular aperture 14 with an elongated cut 26 extending from the aperture 14 to an edge of the pad 10. Other aperture shapes can be sued. The pad 10 also contains cationic substances, such as cationic polymer, cationic proteins on a bottom surface (not shown) of the pad.

Figure 3:
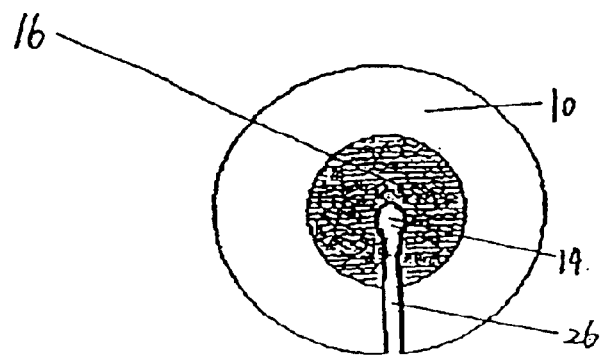
FIG. 3 is a top view of a third embodiment of the present invention showing a central non-slip etched area on a top surface of the pad and an opening, particularly a slit extending from a central aperture to an edge of the pad.

FIG. 3 shows another embodiment of the present invention. Referring to FIG. 3, the pad 10 has a generally circular aperture 14, an elongated cut 26 extending from the aperture 14 to an edge of the pad 10, and a central non-slip etched area 16 on a top surface of pad 10 in order to provide more friction between the finger of the surgeon and the top surface of the pad. The non-slip etched area make it easier to apply a pressure to a puncture site, and make the hemostasis more efficiently and quickly.

Figure 4:
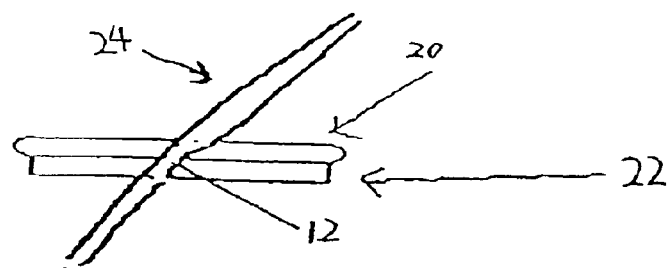
FIG. 4 is a side view of the present invention showing a catheter extending through a disc, wherein the disc having a hemostatic layer attached to a bottom surface of the disc, and an opening permitting egress of the indwelling catheter through the disc.

A disc 20 may be used instead of the pad to effect a uniform pressure on the wound site. The disc 20 may rigid, semi-rigid, or flexible. As shown in FIG. 4, one embodiment of the present invention comprises a disc 20 and a hemostatic layer 22 attached to a bottom surface of the disc. The device also has an opening 12 at an approximately central point of the disc 20. The opening is sized to permit egress of the indwelling catheter 24 or other medical equipment through the disc.

Figure 5:
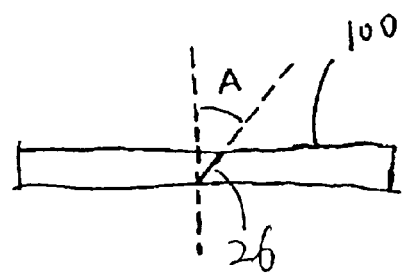
FIG. 5 is a side view of an alternative embodiment of the present invention.

FIG. 5 shows an alternative hemostatic device 100 of the present invention. As shown in FIG. 5, the elongated cut 26 is a bias cut at an angle A with respect to the normal to the upper surface of the pad 100, preferably at 45 degrees, although other angles may be used. With that bias cut through the hemostatic pad 100, the opposing bevel surfaces at the cut form a substantial closure across the cut after the flap adjacent to the cut is lifted to permit passage of a catheter (to the aperture) and then lowered again.

Figure 5A:
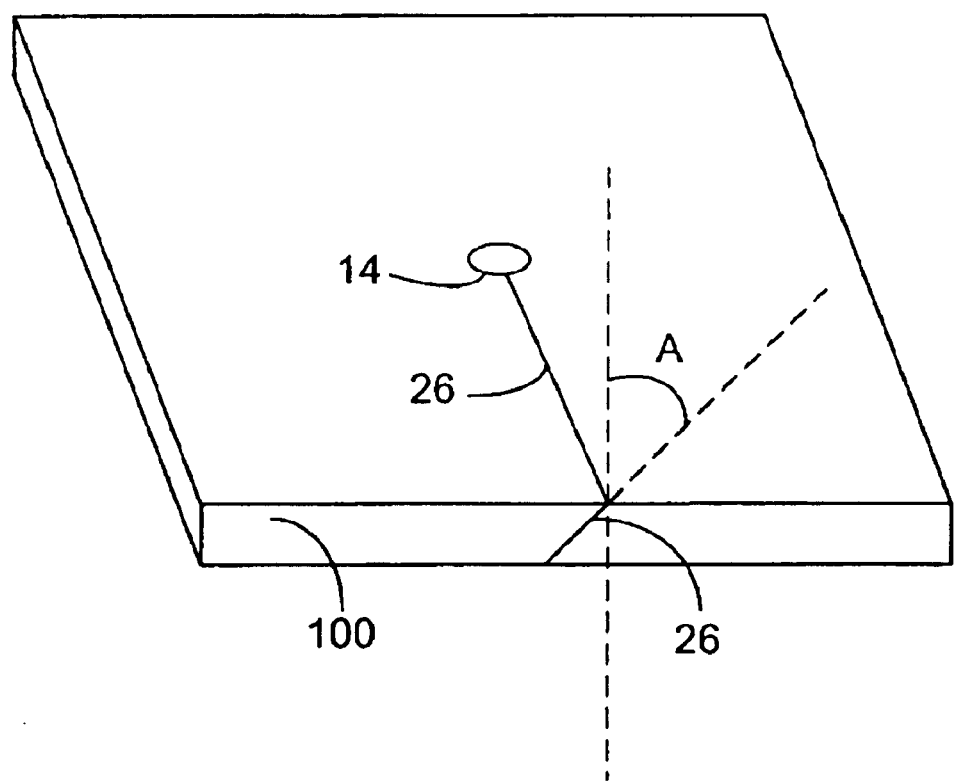
FIG. 5A is a top perspective view of one preferred form of the present invention.

In one preferred form, as shown in FIG. 5A, the elongated bias cut extend from the central aperture defined on the pad.

In a medical procedure, when the hemostatic device is applied to a puncture wound with an indwelling tubular element extending therefrom, the pad with the bias cut and the aperture thereof seal the wound around the indwelling tubular element.

Figure 5B:
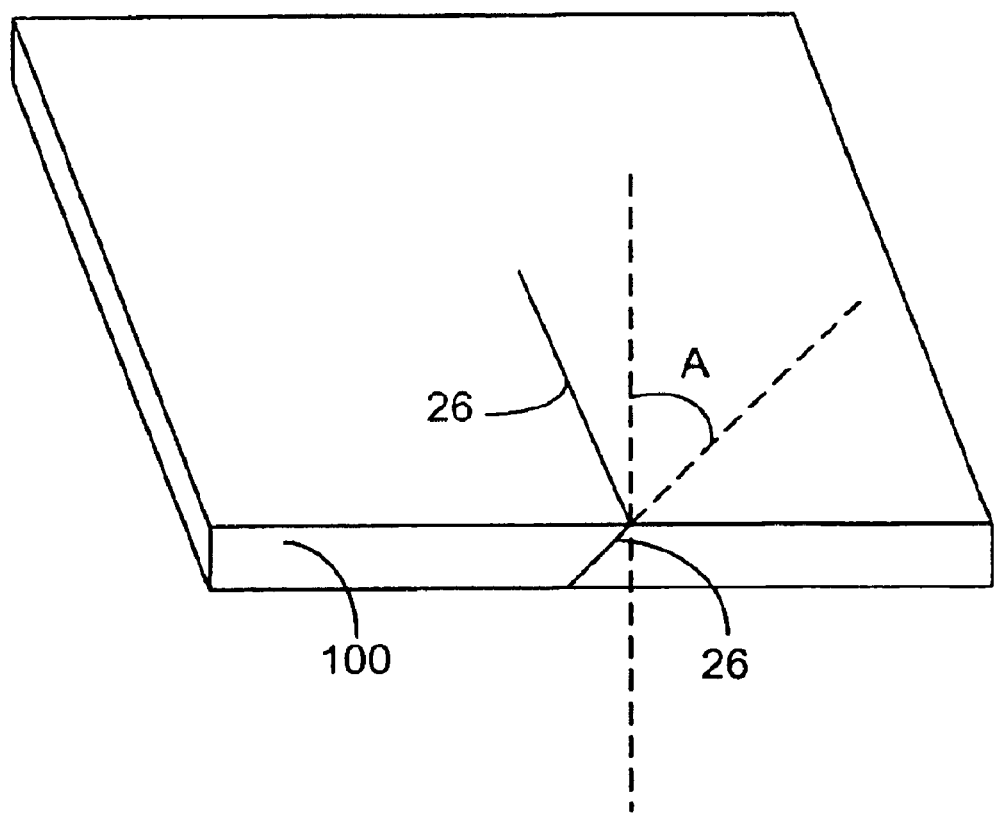
FIG. 5B is a top perspective view of an alternative form of the present invention.

In another preferred form, as shown in FIG. 5B, the hemostatic pad only defines an elongated cut or slit extending from an approximately central point of the pad. The cut or slit is at a bias angle with respect to the normal of the central region of the pad. In a medical procedure, a surgeon can lift the flap adjacent to the cut to allow passage of an indwelling catheter and then locate the hemostatic pad on the wound with the catheter extending through the central point of the pad. After the catheter is removed, the flap close to the central point is lowered and the bevel surfaces at the cut form a substantial closure across the cut. Thereby, the hemostatic pad seals the wound to prevent the wound from exposure to the air.

The method for effecting hemostasis at a puncture wound with an indwelling tubular element extending therethrough includes applying pressure proximal to the puncture wound (not shown) to at least partially collapse the blood vessel (not shown), and directing a cationic application surface of a closure pad 10 against the puncture wound with force sufficient to substantially prevent fluid from exiting the puncture wound, wherein the pad 10 defines an opening 12 therethrough to permit egress of the indwelling tubular element through the pad 10. Then the pressure proximal to the puncture wound is removed. The method then includes maintaining the force on the closure pad 10 and against the wound for at least a first predetermined time period, and removing the force on the closure pad 10 upon verification of hemostasis. Hemostasis is generally verified visually.

The first predetermined time period is substantially proportional to a diameter of the tubular element, and thus the resulting puncture wound In general, however, the first predetermined time period is preferably equal to about ten minutes, although other time periods can be used. In any event, the pressure is not removed from the closure pad 10 and the puncture wound until hemostasis is confirmed. Thus force may need to be maintained on the closure pad 10 for longer than ten minutes. A dressing can comprise gauze pads and tape, or other suitable dressings, placed over the closure pad.

After twenty-four hours, the dressing and the closure pad 10 may be removed from the puncture wound. If hemostasis can not be confirmed after removal of the dressing and the closure pad, a new closure pad and dressing should be applied to the wound, until hemostasis is confirmed.

The method of the present invention provides many benefits, including reducing the time period required to stop bleeding at a puncture wound and decreasing the likelihood that a hematoma will form after removal of a catheter from the puncture wound. The hemostatic substance therefore can be applied evenly, directly and intimately around the catheter, introducer or tube, also permitting the even application of pressure for hemostasis. It also allows for easier removal of the indwelling catheter, introducer or tube through the dressing, pad or device. In addition, the hemostatic pad or device may have a non-slip etched area on the top surface of the pad, in order to provide more friction between the finger of the surgeon and the surface of the pad in order to make the application of pressure to a puncture site more conveniently and allow the puncture site achieve hemostasis more efficiently.

In the above embodiment, the hemostatic agent is preferably a cationic biopolymer of glucosamine. The cationic biopolymer of glucosamine is provided in one or more of the following forms: poly-D-glucosamine; an acetate salt of poly-N-acetylglucosamine; an acetate salt of poly-D-glucosamine; poly-N-acetylglucosamine and poly-D-glucosamine; an acetate salt of poly-N-acetylglucosamine and poly-D-glucosamine; an acetate salt of poly-N-acetylglucosamine and an acetate salt of poly-D-glucosamine; and poly-N-acetylglucosamine and an acetate salt of poly-D-glucosamine. In forms including an acetate salt, the application surface is water soluble. Acidic environments other than an acetate salt, such as lactic acid, can also be incorporated as part of the biopolymer of glucosamine.

In a preferred form, the cationic biopolymer of glucosamine is derived from chitosan, which is a collective term applied to deacetylated chitins in various stages of deacetylation and depolymerization. Chitin is the structural polymer of the exo-skeleton of arthropods and cell walls of fungi, and is composed of poly-N-Acetyl glucosamine units. These are linked by Beta 1–4 glycosidic bonds into a linear polymer containing 2,000 to 3,000 units.

The invention may be embodied in other specific forms without departing from the spirit or essential characteristics thereof. The present embodiments are therefore to be considered in all respects illustrative and not restrictive, the scope of the invention being indicated by the appended claims rather than by the foregoing description, and all changes which come within the meaning and range of equivalency of the claims are therefore intended to be embraced therein.

What is claimed is:

1. A device for effecting hemostasis at a puncture wound with an indwelling tubular element extending therethrough, said device comprising:
   a pad having a top surface and a bottom surface, said pad defining an aperture near a central region thereof adapted for passage therethrough of said tubular element, and an elongated cut extending from said aperture to a peripheral point of said pad, wherein said cut includes a pair of complementary bevel surfaces facing each other and positionable to be in contact with each other, forming an openable substantial closure across the cut; and
   a hemostatically effective amount of a hemostatic agent on said bottom surface of said pad.

2. The device of claim 1, wherein the hemostatic agent comprises a cationic biopolymer of glucosamine.

3. The device of claim 2, wherein the biopolymer of glucosamine is poly-N-acetylglucosamine.

4. The device of claim 1, wherein the tubular element is a catheter.

5. The device of claim 1, wherein the tubular element is an introducer.

6. The device of claim 1, wherein the tubular element is a tube.

7. The device of claim 1, wherein said aperture is at an approximate center of said pad.

8. The device of claim 1, wherein said aperture and said cut form a slit.

9. The device of claim 8, wherein said slit is at a bias angle with respect to the central region of the pad.

10. The device of claim 9, wherein said slit is at a bias angle of about 45 degrees with respect to the central region of the pad.

11. The device of claim 1 further comprising a central non-slip etched area on a top surface of said pad.

12. The device of claim 1, wherein said cut is at a bias angle with respect to the central region of the pad.

13. The device of claim 12, wherein said cut is at a bias angle of about 45 degrees with respect to the central region of the pad.

14. A device for effecting hemostasis at a puncture wound with an indwelling tubular element extending therethrough, said device comprising:

a disc having a hemostatic layer attached to a bottom surface of said disc, wherein said disc defines an aperture through said disc, and wherein said aperture is adapted to permit egress of the indwelling tubular element through said disc, and wherein said disk defines a cut extending from said aperture to a peripheral point of said disc, wherein said cut includes a pair of complementary bevel surfaces facing each other and positionable to be in contact with each other, forming an openable substantial closure across the cut.

15. The device of claim 14, wherein the hemostatic layer comprises a cationic biopolymer of glucosamine.

16. The device of claim 15, wherein the biopolymer of glucosamine is poly-N-acetylglucosamine.

17. The device of claim 14, wherein the tubular element is a catheter.

18. The device of claim 14, wherein the tubular element is an introducer.

19. The device of claim 14, wherein the tubular element is a tube.

20. The device of claim 14, wherein said aperture and said cut form a slit extending from an approximately central point to an edge of said disc.

21. The device of claim 20, wherein said slit is at a bias angle with respect to a central region of the disc.

22. The device of claim 21, wherein said slit is at a bias angle of about 45 degrees with respect to the central region of the disc.

23. The device claim 14 further comprising a central non-slip etched area on a top surface of said disc.

24. The device of claim 14, wherein said cut is at a bias angle with respect to a central region of the disc.

25. The device of claim 24, wherein said cut is at a bias angle of about 45 degrees with respect to the central region of the pad.

26. A device for effecting hemostasis at a puncture wound with an indwelling tubular element extending therethrough, said device comprising:

a pad having a top surface and a bottom surface, said pad defining an aperture near a central region thereof adapted for passage therethrough of said tubular element, and an elongated beveled cut extending from said aperture to a peripheral point of said pad, wherein said cut is at a bias angle with respect to the central region of the pad; and a hemostatically effective amount of a hemostatic agent on said bottom surface of said pad.

27. The device of claim 26, wherein said cut is at a bias angle of about 45 degrees with respect to the central region of the pad.

28. A device for effecting hemostasis at a puncture wound with an indwelling tubular element extending therethrough, said device comprising:

a disc having a hemostatic layer attached to a bottom surface of said disc, wherein said disc defines an aperture through said disc, and wherein said apertute is adapted to permit egress of the indwelling tubular element through said disc, and wherein said disc defines a beveled cut extending from said aperture to a peripheral point of said disc, wherein said cut is at a bias angle with respect to a central region of the disc.

29. The device of claim 28, wherein said cut is at a bias angle of about 45 degrees with respect to the central region of the disc.

* * * * *

UNITED STATES PATENT AND TRADEMARK OFFICE
CERTIFICATE OF CORRECTION

PATENT NO. : 6,890,344 B2
DATED : May 10, 2005
INVENTOR(S) : Melvin Levinson

It is certified that error appears in the above-identified patent and that said Letters Patent is hereby corrected as shown below:

Column 7,
Line 11, after "wherein said", delete "disk", and insert thereof -- disc --; and Column 8,
Line 26, after "wherein said" and before "is", delete "apertute" and insert thereof -- aperture --.

Signed and Sealed this

Twelfth Day of July, 2005

JON W. DUDAS
*Director of the United States Patent and Trademark Office*